(12) United States Patent
Yang et al.

(10) Patent No.: US 11,014,899 B2
(45) Date of Patent: May 25, 2021

(54) METHODS OF DRYING PROPYLENE OXIDE

(71) Applicant: Lyondell Chemical Technology, L.P., Houston, TX (US)

(72) Inventors: Xueyong Yang, Bellaire, TX (US); Daniel F. White, Houston, TX (US); Ha H. Nguyen, Houston, TX (US); Robert J. Rebman, Pearland, TX (US); Chelsee A. Arceneaux, Deer Park, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/931,051

(22) Filed: May 13, 2020

(65) Prior Publication Data
US 2020/0361888 A1 Nov. 19, 2020

Related U.S. Application Data

(60) Provisional application No. 62/848,335, filed on May 15, 2019.

(51) Int. Cl.
*C07D 301/32* (2006.01)

(52) U.S. Cl.
CPC .................. *C07D 301/32* (2013.01)

(58) Field of Classification Search
CPC .................................... C07D 301/32
USPC ......................................... 549/542
See application file for complete search history.

(56) References Cited

U.S. PATENT DOCUMENTS 3,843,488 A * 10/1974 Schmidt et al. ..... C07D 301/32
203/52

FOREIGN PATENT DOCUMENTS

JP 2003160573 A * 6/2003

* cited by examiner

*Primary Examiner* — Taofiq A Solola

(57) ABSTRACT

Methods of drying streams that include propylene oxide. The methods may include contacting a stream that includes propylene oxide with molecular sieves. The molecular sieves may be in a drying unit, and may be regenerated. The streams that include propylene oxide may include one or more other organic compounds.

20 Claims, 3 Drawing Sheets

METHODS OF DRYING PROPYLENE OXIDE

CROSS-REFERENCE TO RELATED APPLICATION

This application claims the benefit of priority to U.S. Provisional Application No. 62/848,335 filed May 15, 2019, which is incorporated here by reference in its entirety.

BACKGROUND

Propylene oxide may be used in a number of processes. For example, refined propylene oxide may be used as a feedstock in processes for producing 1,4-butanediol. The production of 1,4-butanediol may be achieved through the isomerization of propylene oxide to allyl alcohol, which then undergoes hydroformylation with synthesis gas ($H_2$+ CO) to produce 4-hydroxybutyraldehyde, which is hydrogenated to 1,4-butanediol.

Propylene oxide may be created as a product or by-product of a number of processes. Propylene oxide created by such processes may include more water than the refined propylene oxide streams used as a feedstock in certain processes, including the foregoing process for producing 1,4-butanediol. For example, some processes produce samples of propylene oxide having a water content of about 2% by weight.

Efforts to reduce the amount of water in propylene oxide have been based on distillation. Distillation, however, is a thermal separation process, which not ideal as far as energy consumption is concerned.

There remains a need for methods of drying propylene oxide that are energy efficient, are effective, do not cause propylene oxide to react with one or more other compounds, and/or do not undesirably increase the likelihood that propylene oxide may react with one or more other compounds.

BRIEF SUMMARY

Provided herein are methods of drying a stream that includes propylene oxide and water with molecular sieves, including methods that may be energy efficient and/or effective. In some embodiments, the methods minimally, or do not, impact propylene oxide, including its chemical structure and/or reactivity. In some embodiments, the amount of water in the stream is reduced to about 50 ppm.

In one aspect, methods of drying a stream are provided. In some embodiments, the methods include providing a first stream that includes propylene oxide and a first amount of water, and contacting the first stream with a plurality of molecular sieves to form a second stream that includes propylene oxide and a second amount of water. In some embodiments, the first amount of water is greater than the second amount of water. In some embodiments, the methods also include regenerating the molecular sieves.

In some embodiments, the methods include providing a first stream that includes propylene oxide and a first amount of water, wherein the first amount of water constitutes about 1% to about 12%, by weight, of the first stream; providing a molecular sieves drying unit that includes (i) a reservoir having an inlet and an outlet, and (ii) a plurality of molecular sieves in the reservoir; feeding the first stream in the inlet of the reservoir; and collecting a second stream at the outlet of the reservoir; wherein the second stream includes propylene oxide and a second amount of water, wherein the second amount of water constitutes about 50 ppm to about 300 ppm of the second stream. In some embodiments, the feeding of the first stream in the inlet of the reservoir is at a rate effective to achieve a space velocity of about 0.01 $hr^{-1}$ to about 1.0 $hr^{-1}$.

Additional aspects will be set forth in part in the description which follows, and in part will follow naturally from the description, or may be learned by practice of the aspects described below. The advantages described below will be realized and attained by means of the elements and combinations particularly pointed out in the appended claims. It is to be understood that both the foregoing general description and the following detailed description are merely exemplary and explanatory and are not restrictive.

DETAILED DESCRIPTION

Provided herein are methods of drying a stream that includes propylene oxide and water. As used herein, the term "drying" refers to removing at least a portion of water that is present in a stream. In some embodiments, the methods described herein are capable of drying propylene oxide in a manner that is energy efficient, especially compared to other methods. Embodiments of the methods described herein minimally, or do not, impact the propylene oxide, including its reactivity and/or chemical structure.

In some embodiments, the methods herein may include providing a first stream that includes propylene oxide and a first amount of water; and contacting the first stream with a plurality of molecular sieves to form a second stream that includes propylene oxide and a second amount of water, wherein the first amount of water is greater than the second amount of water.

The contacting of the first stream with the plurality of molecular sieves may be achieved by any technique. In some embodiments, the plurality of molecular sieves may be in a reservoir having an inlet and an outlet, and the contacting of the first stream with the plurality of molecular sieves includes feeding the first stream in the inlet of the reservoir. When a plurality of molecular sieves is in a reservoir, the resulting apparatus may be referred to herein as a "molecular sieves drying unit." The feeding of the first stream in the inlet of the reservoir may be performed and/or assisted by an apparatus, such as a pump.

The reservoir may have any shape. In some embodiments, the reservoir is cylindrical. In some embodiments, the reservoir is cylindrical, and has one or more tapered ends. The reservoir also may have any volume that is sufficient to accommodate the plurality of molecular sieves. In some embodiments, the volume of the reservoir equals or exceeds by about 0.1% to about 10% the minimum volume occupied by the plurality of molecular sieves.

The reservoir may have an inlet and an outlet. The reservoir may have a first end and a second end, and the inlet and outlet may be arranged at or near the first end and second end, respectively. In some embodiments, the inlet and outlet are located at positions that increase and/or maximize a residence time of a stream in the reservoir, increase and/or maximize the percentage of molecular sieve(s) contacted by a stream, or a combination thereof.

Figure 1:
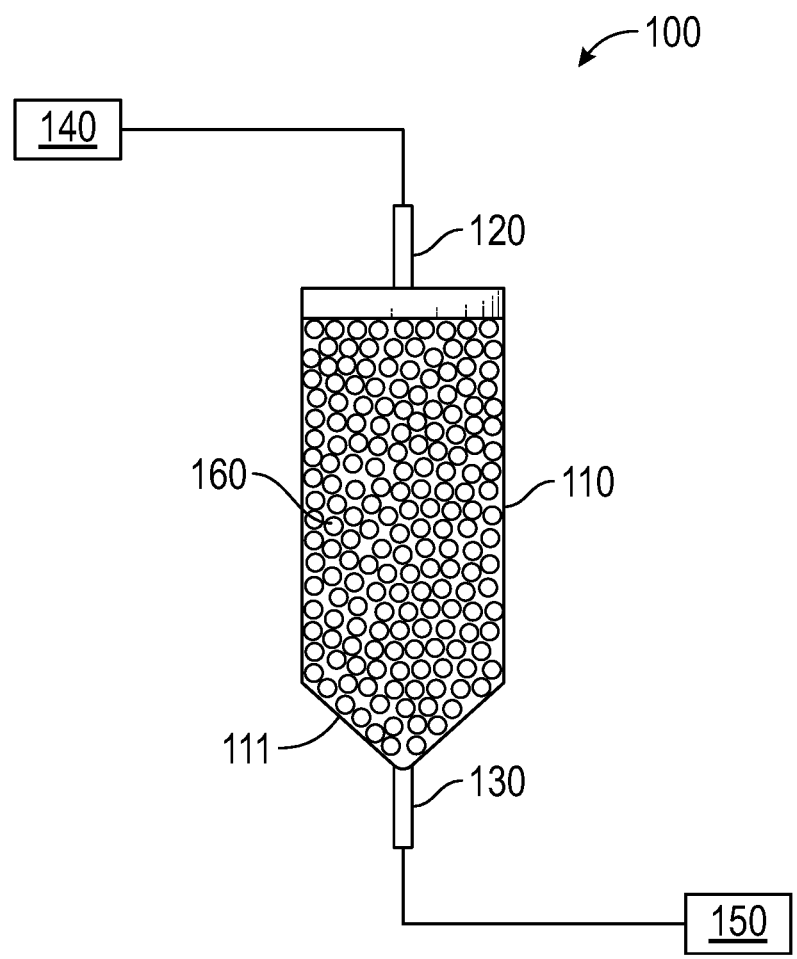
FIG. 1 depicts an embodiment of a molecular sieves drying unit.

An embodiment of a molecular sieves drying unit is depicted at FIG. 1. The molecular sieves drying unit 100 of FIG. 1 includes a reservoir 110, which, in this embodiment, is made of a transparent material (e.g., glass, plastic, etc.). The reservoir 110 is cylindrical, and has a tapered end 111. The reservoir 110 also includes an inlet 120 and an outlet 130, which are arranged at opposite ends of the reservoir 110. In the reservoir 110 is a plurality of molecular sieves 160. Although the volume occupied by the plurality of molecular sieves 160 roughly corresponds with the volume of the reservoir 110, other configurations are possible. For example, the plurality of molecular sieves 160, in other embodiments, may occupy a fraction (e.g., ½, ¾, etc.) of the volume of the reservoir 110. A first stream 140 that includes propylene oxide and a first amount of water is fed in the reservoir 110 via the inlet 120, and a second stream 150 that includes propylene oxide and a second amount of water exits the reservoir 110 via the outlet 130.

A first stream may be fed in the inlet of a reservoir at any rate that is effective to dry a stream. The rate may be static, dynamic, or a combination thereof. For example, a first stream may be fed at a static rate during a first portion of a method, and then the rate may be decreased during a second portion of a method.

In some embodiments, a rate at which the first stream is fed in the inlet is effective to achieve a space velocity (mass flowrate of first stream/mass of plurality of molecular sieves) of about 0.01 $hr^{-1}$ to about 1.0 $hr^{-1}$. In some embodiments, a rate at which the first stream is fed in the inlet is effective to achieve a space velocity of about 0.1 $hr^{-1}$ to about 1.0 $hr^{-1}$. In some embodiments, a rate at which the first stream is fed in the inlet is effective to achieve a space velocity of about 0.2 $hr^{-1}$ to about 1.0 $hr^{-1}$. In some embodiments, a rate at which the first stream is fed in the inlet is effective to achieve a space velocity of about 0.3 $hr^{-1}$ to about 1.0 $hr^{-1}$. In some embodiments, a rate at which the first stream is fed in the inlet is effective to achieve a space velocity of about 0.4 $hr^{-1}$ to about 1.0 $hr^{-1}$. In some embodiments, a rate at which the first stream is fed in the inlet is effective to achieve a space velocity of about 0.5 $hr^{-1}$ to about 1.0 $hr^{-1}$. In some embodiments, a rate at which the first stream is fed in the inlet is effective to achieve a space velocity of about 0.6 $hr^{-1}$ to about 1.0 $hr^{-1}$. In some embodiments, a rate at which the first stream is fed in the inlet is effective to achieve a space velocity of about 0.7 $hr^{-1}$ to about 1.0 $hr^{-1}$. In some embodiments, a rate at which the first stream is fed in the inlet is effective to achieve a space velocity of about 0.8 $hr^{-1}$ to about 1.0 $hr^{-1}$. In some embodiments, a rate at which the first stream is fed in the inlet is effective to achieve a space velocity of about 0.9 $hr^{-1}$ to about 1.0 $hr^{-1}$.

When a plurality of molecular sieves is in a reservoir, the reservoir may be subjected to any temperature and/or any pressure. In some embodiments, a reservoir is at ambient temperature during the methods described herein. A reservoir is at ambient temperature when no effort is made to influence a temperature of the reservoir; for example, a reservoir is not placed in or near a heating or cooling apparatus. It should be noted that a temperature of a reservoir may be modified by the heat of adsorption as water molecules adsorb to the plurality of molecular sieves. Due to the heat of adsorption, a reservoir at ambient temperature, as defined herein, may have a temperature that is slightly greater than the temperature of the environment in which the reservoir is used. Therefore, as used herein, the phrase "ambient temperature" includes [1] a temperature of a reservoir when no effort is made to modify the temperature of the reservoir, and [2] a temperature that results from one or more features of the processes described herein, such as the heat of adsorption that is generated as the water molecules adsorb to the plurality of molecular sieves.

In some embodiments, the reservoir is subjected to a temperature greater than an ambient temperature. The temperature greater than an ambient temperature may be achieved by any technique, such as placing the reservoir in or near a heating apparatus. The heating apparatus may include a heated oil bath in which a reservoir is at least partially submerged, a heated wrap that is adjacent to and/or contacts at least a portion of an outer surface of the reservoir, a heat source placed near a reservoir, or a combination thereof.

In some embodiments, the reservoir is subjected to a temperature less than an ambient temperature. The temperature less than an ambient temperature may be achieved by any technique, such as placing the reservoir in or near a cooling apparatus. The cooling apparatus may include a cooled bath (e.g., an ice bath) in which a reservoir is at least partially submerged, a cooling source placed at or near a reservoir, or a combination thereof.

The plurality of molecular sieves used in the methods described herein may be regenerated. As used herein, the terms "regenerated", "regenerating", "regeneration" and the like refer to the elimination or lessening of an amount of water that is adsorbed to a plurality of molecular sieves. The regeneration of molecular sieves may increase their effectiveness, as the regeneration may increase the area of the molecular sieves to which water molecules may adsorb.

In some embodiments, the regenerating of the plurality of molecular sieves includes (i) heating the plurality of molecular sieves at a temperature for a time effective to regenerate the plurality of molecular sieves, (ii) heating the plurality of molecular sieves under vacuum at the temperature for the time effective to regenerate the plurality of molecular sieves, (iii) heating the plurality of molecular sieves at the temperature for the time effective to regenerate the plurality of molecular sieves and contacting the plurality of molecular sieves with a carrier gas, or (iv) a combination thereof. The carrier gas may be an inert gas, a dry (or nearly dry) gas, or a combination thereof. For example, nitrogen ($N_2$), argon, or a combination thereof may be used.

First Stream

The methods described herein may include providing a first stream that includes propylene oxide and a first amount of water.

The first stream may be a stream that is produced by a chemical process, such as a chemical process that produces propylene oxide as a product or by-product.

Not wishing to be bound by any particular theory, it is believed that a mixture of propylene oxide and water can include up about 12.6%, by weight, of water before phase separation may occur. Therefore, in the first streams described herein, the weight ratio of propylene oxide to the first amount of water may be about 87.4:12.6 to about 99.999:0.001.

In some embodiments, for the first stream, the weight ratio of propylene oxide to the first amount of water is about 88:12 to about 99:1. In some embodiments, for the first stream, the weight ratio of propylene oxide to the first amount of water is about 90:10 to about 99:1. In some embodiments, for the first stream, the weight ratio of propylene oxide to the first amount of water is about 95:5 to about 99:1. In some embodiments, for the first stream, the weight ratio of propylene oxide to the first amount of water is about 97:3 to about 99:1.

In some embodiments, the first stream includes at least one third compound (i.e., a compound other than propylene oxide and water). The at least one third compound may include any compound that does not undesirably impact the methods described herein.

In some embodiments, the first stream includes an organic compound (i.e., an organic compound other than propylene oxide). The organic compound may include one or more hydrocarbons (e.g., $C_4$-$C_6$ hydrocarbons, such as 2-methyl-pentane), one or more oxygen-containing compounds (e.g., propionaldehyde, methanol, acetone, methyl formate and aldehydes), or a combination thereof. The organic compound may be present in the first stream at an amount of about 0.001% to about 10%, by weight, of the first stream, about 0.001% to about 8%, by weight, of the first stream, about 0.001% to about 6%, by weight, of the first stream, about 0.001% to about 5%, by weight, of the first stream, about 0.001% to about 4%, by weight, of the first stream, about 0.001% to about 2%, by weight, of the first stream, or about 0.001% to about 1%, by weight, of the first stream.

In some embodiments, the organic compound is a polar organic compound, such as acetone. In some embodiments, the organic compound is a non-polar organic compound, such as a hydrocarbon. For example, the hydrocarbon may include 2-methyl-pentane. In some embodiments, the organic compound includes at least one polar organic compound and at least one non-polar organic compound. The methods described herein, in some embodiments, are not undesirably impacted by the presence of an organic compound (i.e., an organic compound other than propylene oxide) in the first stream.

In some embodiments, the first amount of water in the first stream constitutes about 0.001% to about 12%, by weight, of the first stream. In some embodiments, the first amount of water in the first stream constitutes about 1% to about 12%, by weight, of the first stream. In some embodiments, the first amount of water in the first stream constitutes about 1% to about 10%, by weight, of the first stream. In some embodiments, the first amount of water in the first stream constitutes about 1% to about 8%, by weight, of the first stream. In some embodiments, the first amount of water in the first stream constitutes about 1% to about 5%, by weight, of the first stream. In some embodiments, the first amount of water in the first stream constitutes about 1% to about 4%, by weight, of the first stream. In some embodiments, the first amount of water in the first stream constitutes about 1% to about 3%, by weight, of the first stream.

Second Stream

The methods described herein may produce a second stream that includes propylene oxide and a second amount of water. The first amount of water, which is present in the first stream, may be greater than the second amount of water, which is present in the second stream. In some embodiments, the first stream and the second stream may be similar, except for the difference between the first amount of water and the second amount of water.

In some embodiments, the second amount of water constitutes 0.1%, by weight, or less of the second stream. Therefore, the second stream may include propylene oxide and about 0.1%, by weight, or less of water; or the second stream may include propylene oxide, one or more third compounds (e.g., an organic compound other than propylene oxide), and about 0.1%, by weight, or less of water.

In some embodiments, the second amount of water constitutes about 10 ppm to about 500 ppm of the second stream. Therefore, the second stream may include propylene oxide and about 10 ppm to about 500 ppm water; or the second stream may include propylene oxide, one or more third compounds (e.g., an organic compound other than propylene oxide), and about 10 ppm to about 500 ppm water. In some embodiments, the second amount of water constitutes about 50 ppm to about 300 ppm of the second stream. In some embodiments, the second amount of water constitutes about 10 ppm to about 400 ppm of the second stream. In some embodiments, the second amount of water constitutes about 100 ppm to about 400 ppm of the second stream. In some embodiments, the second amount of water constitutes about 100 ppm to about 300 ppm of the second stream. In some embodiments, the second amount of water constitutes about 100 ppm to about 200 ppm of the second stream.

Molecular Sieves

As used herein, the phrase "a plurality of molecular sieves" refers to a collection of porous particles, wherein the porous particles are configured to adsorb molecules (e.g., water molecules) of a specific size. The phrase "a plurality of molecular sieves" includes, but is not limited to, a monolithic structure comprised of one or more individual molecular sieves.

In some embodiments, the plurality of molecular sieves used in the methods described herein include crystalline metal aluminosilicates having a three-dimensional interconnecting network of silica and alumina tetrahedra.

In some embodiments, the plurality of molecular sieves includes "3 A" molecular sieves, which have an average pore diameter of about 3 Å. In some embodiments, the plurality of molecule sieves includes "4 A" molecular sieves, which have an average pore diameter of about 4 Å. In some embodiments, the plurality of molecular sieves includes "3 A" molecular sieves, which have an average pore diameter of about 3 Å, and "4 A" molecular sieves, which have an average pore diameter of about 4 Å.

The plurality of molecular sieves may have any average particle size and/or shape. In some embodiments, the plurality of molecular sieves includes spherical particles and/or sphere-like particles. In some embodiments, the plurality of molecular sieves may have a similar average particles size. In some embodiments, the plurality of molecular sieves may have a similar shape. In some embodiments, the plurality of molecular sieves may have both a similar average particle size and a similar shape. In some embodiments, the plurality of molecular sieves have an average particle size of 8 mesh to 12 mesh (i.e., 1.68 mm to 2.38 mm).

The plurality of molecular sieves may have an initial water adsorption capacity of at least 10%, at least 15%, at least 20%, at least 25%, at least 30%, at least 35%, or at least 40%, by weight, at 25° C. The plurality of molecular sieves may have an initial water adsorption capacity of about 10% to about 40%, about 15% to about 40%, about 20% to about 40%, about 25% to about 40%, about 30% to about 40%, or about 35% to about 40%, by weight, at 25° C. The phrase "initial water adsorption capacity" refers to the water absorption capacity of a plurality of molecular sieves prior to a first regeneration. A first regeneration of a plurality of molecular sieves may result in a water adsorption capacity that is equal to or less than an initial water adsorption capacity, and each subsequent regeneration may have a similar impact on water adsorption capacity. In some embodiments, regeneration reduces (i) an initial water adsorption capacity or (ii) a water adsorption capacity of a plurality of molecule sieves previously subjected to one or more regenerations by about 0 to about 10%, or about 0 to about 5%.

As used herein, "PO90" generally comprises, by weight, at least 90% propylene oxide, 1.5-3% water, and one or more impurities (i.e., components other than propylene oxide). The one or more impurities may include: one or more: hydrocarbons (e.g., $C_4$-$C_6$ hydrocarbons, such as 2-methylpentane or isobutylene), oxygen-containing compounds (e.g., propionaldehyde, methanol, acetone, methyl formate, aldehydes, or a combination thereof), or combinations thereof.

In the descriptions provided herein, the terms "includes," "is," "containing," "having," and "comprises" are used in an open-ended fashion, and thus should be interpreted to mean "including, but not limited to." When methods are claimed or described in terms of "comprising" or "including" various elements or feature, the methods can also "consist essentially of" or "consist of" the various components or features, unless stated otherwise.

The terms "a," "an," and "the" are intended to include plural alternatives, e.g., at least one. For instance, the disclosure of "a first stream," "a molecular sieves drying unit," "an organic compound", and the like, is meant to encompass one, or mixtures or combinations of more than one first stream, molecular sieves drying unit, or organic compound, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, numerical end points of ranges disclosed herein are approximate. As a representative example, Applicant discloses, in some embodiments, that a rate at which the first stream is fed in the inlet is effective to achieve a space velocity of about 0.5 $hr^{-1}$ to about 1.0 $hr^{-1}$. This disclosure should be interpreted as encompassing values of about 0.5 $hr^{-1}$ to about 1.0 $hr^{-1}$, and further encompasses "about" each of 0.6 $hr^{-1}$, 0.7 $hr^{-1}$, 0.8 $hr^{-1}$, and 0.9 $hr^{-1}$, including any ranges and sub-ranges between any of these values.

The present embodiments are illustrated herein by referring to various embodiments, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present embodiments or the scope of the appended claims. Thus, other aspects of the embodiments will be apparent to those skilled in the art from consideration of the specification and practice of the embodiments disclosed herein.

EXAMPLES

The present method(s) are further illustrated by the following examples, which are not to be construed in any way as imposing limitations upon the scope thereof. On the contrary, it is to be understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects of this disclosure will be apparent to those skilled in the art from consideration of the specification and practice of the method(s) disclosed herein.

Example 1—Drying of Propylene Oxide

In this example, a 50 g sample was prepared by mixing propylene oxide and water. Prior to drying, the sample included 88.7%, by weight, propylene oxide, and 11.3%, by weight, water.

The sample including propylene oxide (88.7% by weight) and water (11.3% by weight) was placed in a glass bottle that contained 40 g of fresh 3 A molecular sieves. The glass bottle was kept at ambient temperature and ambient pressure; in other words, no pressure was applied to the unit, and the temperature of the unit was not increased beyond whatever increase may have been imparted by the heat of adsorption.

The amount of water in the sample was reduced to 500 ppm after a few hours, and then further reduced to 350 ppm after the sample was left in the glass bottle and in contact with the molecular sieves overnight.

Example 2—Drying of Propylene Oxide Stream

In this example, a stream including propylene oxide and water was dried with a molecular sieves drying unit.

Prior to drying the stream included 97%, by weight, propylene oxide, and 3%, by weight, water.

The molecular sieves drying unit of this example included a cylindrical column that included 60 g of 3 A molecular sieves.

The stream containing propylene oxide (97% by weight) and water (3% by weight) was pumped through the molecular sieves drying unit at a rate of 3 mL per minute. The molecular sieves drying unit was operated at ambient temperature and ambient pressure; in other words, no pressure was applied to the unit other than the pressure imparted by the flow rate, and the temperature of the unit was not increased beyond whatever increase may have been imparted by the heat of adsorption.

In total, four runs were performed in this example, wherein each run included pumping 400 mL of the stream through the molecular sieves drying unit. The first run was performed with fresh molecular sieves, while runs two through four were performed with the spent molecular sieves. As each stream was pumped through the molecular sieves drying unit, the water content of the streams was tested at the intervals depicted at FIG. 2.

Figure 2:
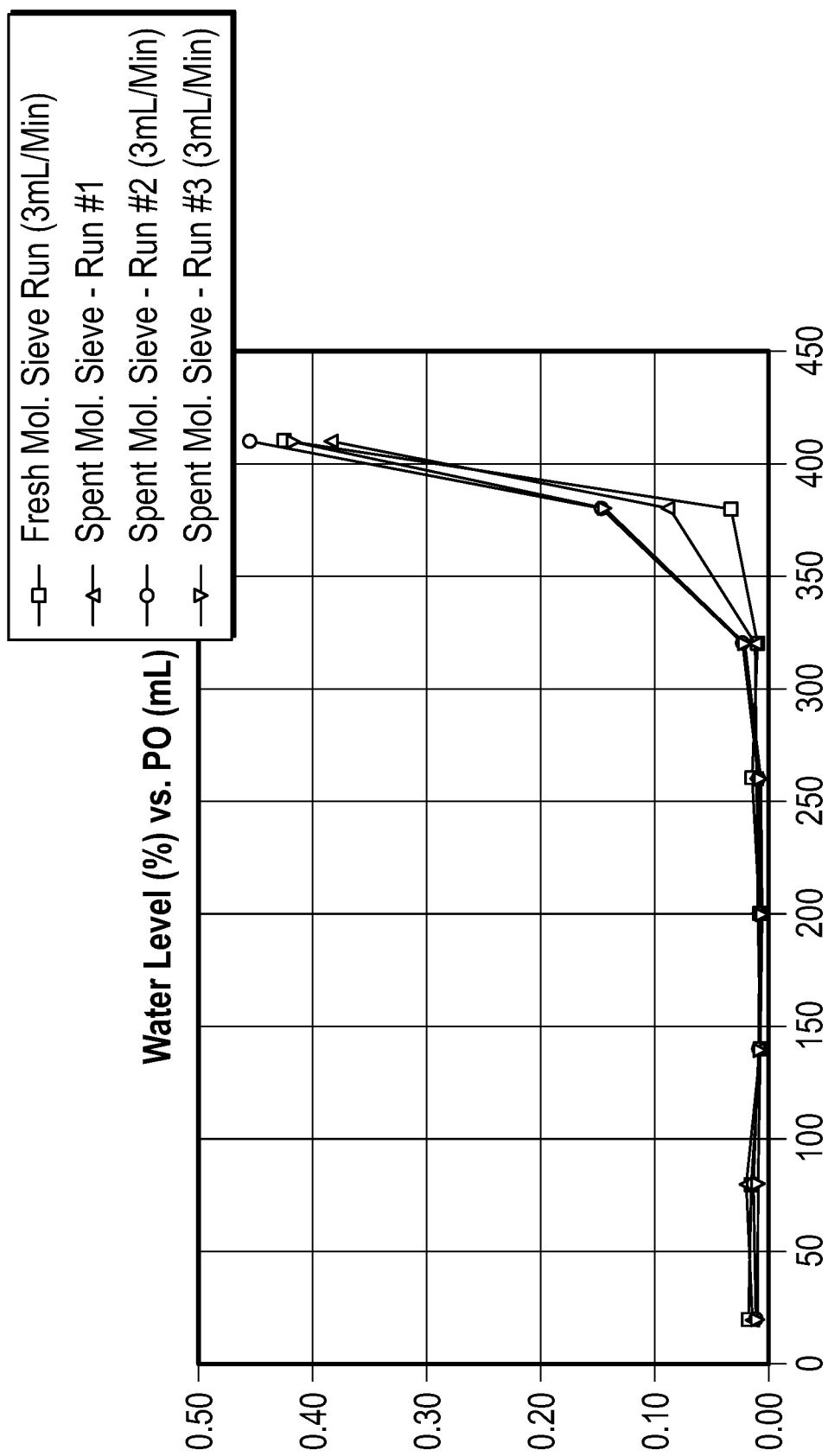
FIG. 2 depicts a plot of water content (wt. %) versus an amount of propylene oxide (PO) passed through an embodiment of a molecular sieves drying unit.

The results of FIG. 2 indicate that the water content of the stream was reduced from 3%, by weight, to about 150 ppm for the first 325 mL of the stream. The results indicate that the performance of molecular sieves decreased after about 350 mL of the stream had been pumped through the molecular sieves drying unit, thereby providing a guide as to how the mass of molecular sieves should be adjusted to accommodate larger volumes of a stream.

Example 3—Molecular Sieve Regeneration

The molecular sieves of the molecular sieves drying unit of Example 2 were regenerated in this example. The molecular sieves, under a nitrogen gas purge, were heated to 260° C. for about 12 hours to about 24 hours.

Increased heating times may be employed if the temperature is greater than 260° C., or, conversely, decreased heating times may be employed if the temperature is less than 260° C.

Example 4—Drying of Propylene Oxide Stream

In this example, a stream including propylene oxide and water was dried with a molecular sieves drying unit that included the regenerated molecular sieves of Example 3.

The stream, prior to drying, included, by weight, 96.5% propylene oxide, 2.4% water, 0.4% hydrocarbon/isobutylene, 0.34% 2-methylpentane, and 0.35% other hydrocarbon/oxygen-containing compounds.

The molecular sieves drying unit of Example 2 was used, and the drying unit included the molecular sieves of Example 2 that had been regenerated by the process of Example 3.

The stream was pumped through the molecular sieves drying unit at a rate of 3 mL per minute. The molecular sieves drying unit was operated at ambient temperature and ambient pressure; in other words, no pressure was applied to the unit other than the pressure imparted by the flow rate, and the temperature of the unit was not increased beyond whatever increase may have been imparted by the heat of adsorption.

In total, four runs were performed in this example, wherein each run included pumping about 550 mL of the stream through the molecular sieves drying unit. The first run was performed with fresh molecular sieves, while runs two through four were performed with the spent molecular sieves. As each stream was pumped through the molecular sieves drying unit, the water content of the streams was tested at the intervals depicted at FIG. 3.

Figure 3:
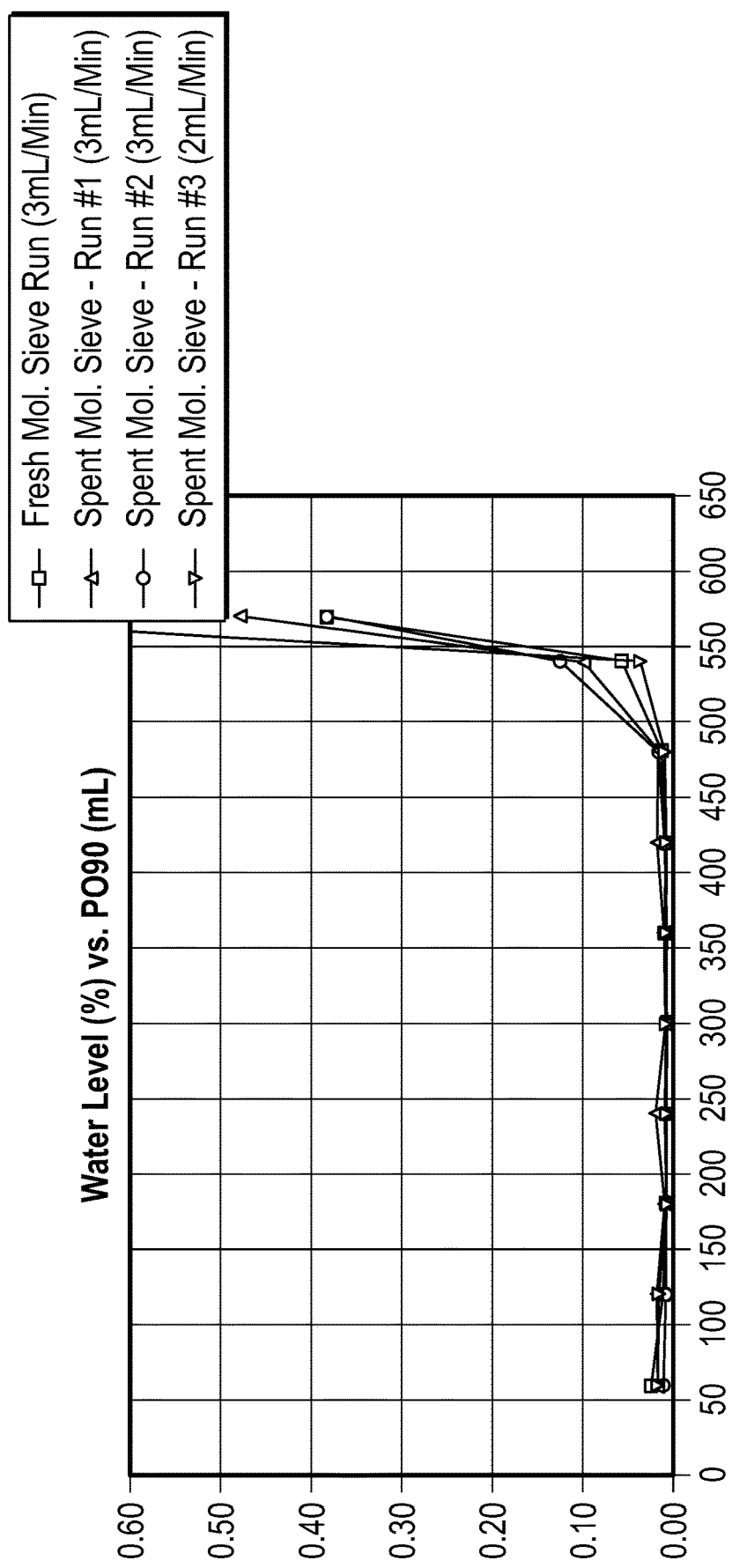
FIG. 3 depicts a plot of water content (wt. %) versus an amount of propylene oxide (PO) passed through an embodiment of a molecular sieves drying unit that included regenerated molecular sieves.

The results of FIG. 3 indicate that the performance of the regenerated molecular sieves of this example improves relative to the performance of the molecular sieves of Example 2.

Example 5—Effect of Other Hydrocarbons

The tests of this example were designed to determine whether the presence of one or more hydrocarbons other than propylene oxide in a stream might undesirably impact water removal.

In this example, two classes of feed samples were tested. The first class consists of a "pure" feed sample in which propylene oxide and water accounted for at least 99.9% of its weight (indicated as "PO" in the following table). The second class consists of PO90 having, by weight, the specified water content as provided in the table below, 0.4% hydrocarbon/isobutylene, 0.34% 2-methylpentane, and 0.35% other hydrocarbon/oxygen-containing compounds with the balance of the feed sample being propylene oxide (from about 96.4 to about 96.6%).

The parameters and results of the tests of this example are depicted in the following table:

Results of Example 5

| Run No. | Feed Sample (% by weight $H_2O$) | Flow Rate (mL/Min) | Total Dried Propylene Oxide (PO) (mL) (0.1% water or less) | Mol. Sieve Status/Type/Amount |
|---|---|---|---|---|
| 1 | PO with 3.1% $H_2O$ | 3.0 | 360 | Fresh 3Å Mol. Sieve: 60.2 g |
| 2 | PO with 2.8% $H_2O$ | 3.0 | 360 | Spent 3Å Mol. Sieve: 60.2 g |
| 3 | PO with 2.9% $H_2O$ | 3.0 | 300 | Spent 3Å Mol. Sieve: 60.2 g |
| 4 | PO with 3.0% $H_2O$ | 3.0 | 300 | Spent 3Å Mol. Sieve: 60.2 g |
| 5 | PO with 3.0% $H_2O$ | 3.0 | 240 | Spent 3Å Mol. Sieve: 60.2 g |
| 6 | PO90 with 2.3% $H_2O$ | 3.0 | 480 | Fresh 3Å Mol. Sieve: 60.1 g |
| 7 | PO90 with 2.4% $H_2O$ | 3.0 | 480 | Spent 3Å Mol. Sieve: 60.1 g |
| 8 | PO90 with 2.4% $H_2O$ | 3.0 | 420 | Spent 3Å Mol. Sieve: 60.1 g |
| 9 | PO90 with 2.4% $H_2O$ | 3.0 | 420 | Spent 3Å Mol. Sieve: 60.1 g |
| 10 | PO90 with 2.3% $H_2O$ | 2.0 | 480 | Spent 3Å Mol. Sieve: 60.1 g |
| 11 | PO90 with 2.5% $H_2O$ | 4.5 | 360 | Spent 3Å Mol. Sieve: 60.1 g |
| 12 | PO90 with 2.3% $H_2O$ | 6.0 | 360 | Spent 3Å Mol. Sieve: 60.1 g |
| 13 | PO90 with 2.3% $H_2O$ | 10.0 | 60 | Spent 3Å Mol. Sieve: 60.1 g |

The data of the foregoing table indicate the presence of an additional organic compound did not undesirably impact the water removal of this example.

The invention claimed is:

1. A method of drying, the method comprising:
   providing a first stream comprising propylene oxide and a first amount of water, wherein the first amount of water constitutes about 1% to about 12%, by weight, of the first stream; and
   contacting the first stream with a plurality of molecular sieves to form a second stream comprising propylene oxide and a second amount of water;
   wherein the second amount of water constitutes about 10 ppm to about 500 ppm of the second stream.

2. The method of claim 1, wherein the plurality of molecular sieves are in a reservoir having an inlet and an outlet, and the contacting of the first stream with the plurality of molecular sieves comprises feeding the first stream in the inlet of the reservoir.

3. The method of claim 2, wherein a rate at which the first stream is fed in the inlet is effective to achieve a space velocity of about 0.01 $hr^{-1}$ to about 1.0 $hr^{-1}$.

4. The method of claim 2, wherein a rate at which the first stream is fed in the inlet is effective to achieve a space velocity of about 0.5 $hr^{-1}$ to about 1.0 $hr^{-1}$.

5. The method of claim 2, wherein the reservoir is at ambient temperature and ambient pressure.

6. The method of claim 1, wherein, in the first stream, the weight ratio of propylene oxide to the first amount of water is about 88:12 to about 99:1.

7. The method of claim 1, wherein, in the first stream, the weight ratio of propylene oxide to the first amount of water is about 97:3 to about 99:1.

8. The method of claim 1, wherein the first amount of water constitutes about 1% to about 10%, by weight, of the first stream.

9. The method of claim 1, wherein the first stream further comprises an organic compound, wherein the organic compound is present in the first stream at an amount of about 0.001% to about 10%, by weight, of the first stream.

10. The method of claim 9, wherein the organic compound comprises a hydrocarbon.

11. The method of claim 10, wherein the hydrocarbon comprises 2-methyl-pentane.

12. The method of claim 1, wherein the second amount of water constitutes about 50 ppm to about 300 ppm of the second stream.

13. The method of claim 1, wherein the second amount of water constitutes about 100 ppm to about 200 ppm of the second stream.

14. The method of claim 1, wherein the plurality of molecule sieves have an average pore diameter of about 3 Å.

15. The method of claim 1, further comprising regenerating the plurality of molecular sieves.

16. The method of claim 15, wherein the regenerating of the plurality of molecular sieves comprises (i) heating the plurality of molecular sieves at a temperature for a time effective to regenerate the plurality of molecular sieves, (ii) heating the plurality of molecular sieves under vacuum at the temperature for the time effective to regenerate the plurality of molecular sieves, (iii) heating the plurality of molecular sieves at the temperature for the time effective to regenerate the plurality of molecular sieves and contacting the plurality of molecular sieves with a carrier gas, or (iv) a combination thereof.

17. A method of drying, the method comprising:
providing a first stream comprising propylene oxide and a first amount of water, wherein the first amount of water constitutes about 1% to about 12%, by weight, of the first stream;
providing a molecular sieves drying unit comprising (i) a reservoir having an inlet and an outlet, and (ii) a plurality of molecular sieves in the reservoir, wherein the plurality of molecular sieves have an average pore diameter of about 3 Å;
feeding the first stream in the inlet of the reservoir at a rate effective to achieve a space velocity of about 0.01 $hr^{-1}$ to about 1.0 $hr^{-1}$; and
collecting a second stream at the outlet of the reservoir;
wherein the second stream comprises propylene oxide and a second amount of water, wherein the second amount of water constitutes about 50 ppm to about 300 ppm of the second stream.

18. The method of claim 17, further comprising regenerating the plurality of molecular sieves.

19. The method of claim 17, wherein the first stream further comprises an organic compound, wherein the organic compound is present in the first stream at an amount of about 0.001% to about 10%, by weight, of the first stream.

20. The method of claim 19, wherein the organic compound comprises 2-methyl-pentane, acetone, or a combination thereof.

* * * * *